(12) United States Patent
Imura

(10) Patent No.: US 7,369,244 B2
(45) Date of Patent: May 6, 2008

(54) OPTICAL MEASURING APPARATUS, ILLUMINATION SYSTEM, AND LIGHT DETECTING SYSTEM

(75) Inventor: Kenji Imura, Toyohashi (JP)

(73) Assignee: Konica Minolta Sensing, Inc., Osaka (JP)

( * ) Notice: Subject to any disclaimer, the term of this patent is extended or adjusted under 35 U.S.C. 154(b) by 345 days.

(21) Appl. No.: 11/273,912

(22) Filed: Nov. 15, 2005

(65) Prior Publication Data

US 2006/0109474 A1 May 25, 2006

(30) Foreign Application Priority Data

Nov. 19, 2004 (JP) .............................. 2004-335759

(51) Int. Cl.
*G01N 21/47* (2006.01)
*G01J 3/46* (2006.01)

(52) U.S. Cl. ...................................... 356/446; 356/402

(58) Field of Classification Search ..................... None
See application file for complete search history.

(56) References Cited

U.S. PATENT DOCUMENTS 6,707,553 B1  3/2004  Imura

*Primary Examiner*—Gregory J. Toatley, Jr.
*Assistant Examiner*—Amanda H Merlino
(74) *Attorney, Agent, or Firm*—Brinks Hofer Gilson & Lione

(57) ABSTRACT

An optical measuring apparatus includes: an illumination system having a toroidal mirror which is by circularly rotating a parabolic curve or its approximate curve around an axis with the focal point of the parabolic curve or the substantial light focusing point of the approximate curve forming a focal point arc; and a plurality of illuminators which are arranged in the vicinity of the focal point arc to reflect beams emanated from the illuminators by the toroidal mirror as parallel beams for projection onto the object surface in different directions on the measurement plane; a light detecting system which detects the reflection beams from the object surface in a specific direction; and a controller/calculator which successively turns on the illuminators, measures the reflection beams from the object surface in respective illuminating directions of the illuminators, and calculates reflection characteristics of the object surface in the respective illuminating directions.

9 Claims, 11 Drawing Sheets

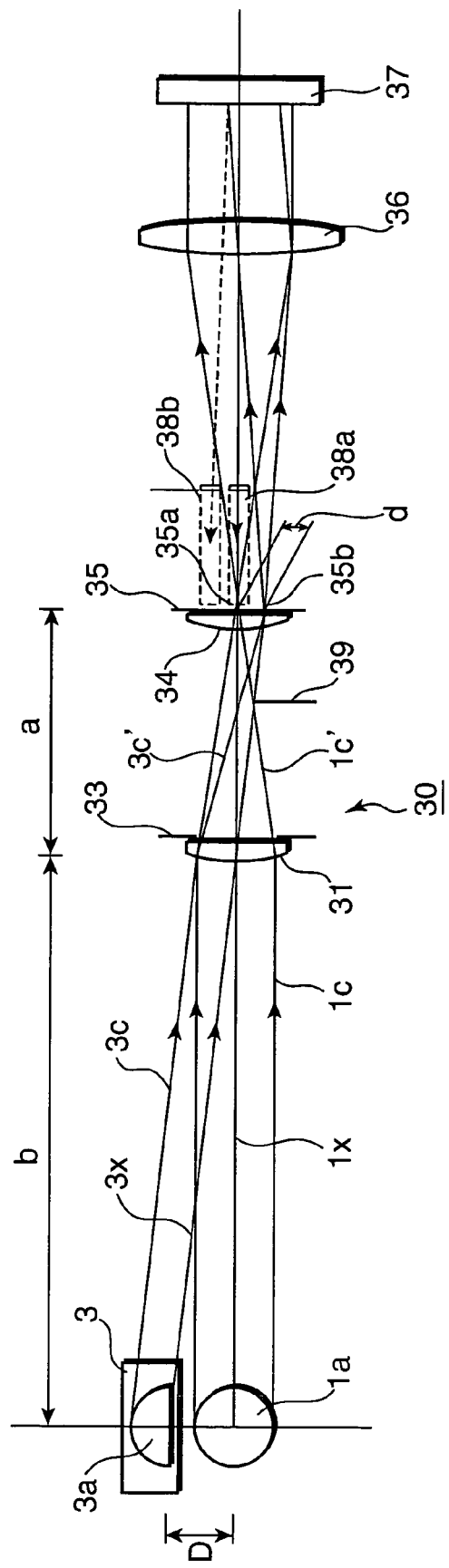

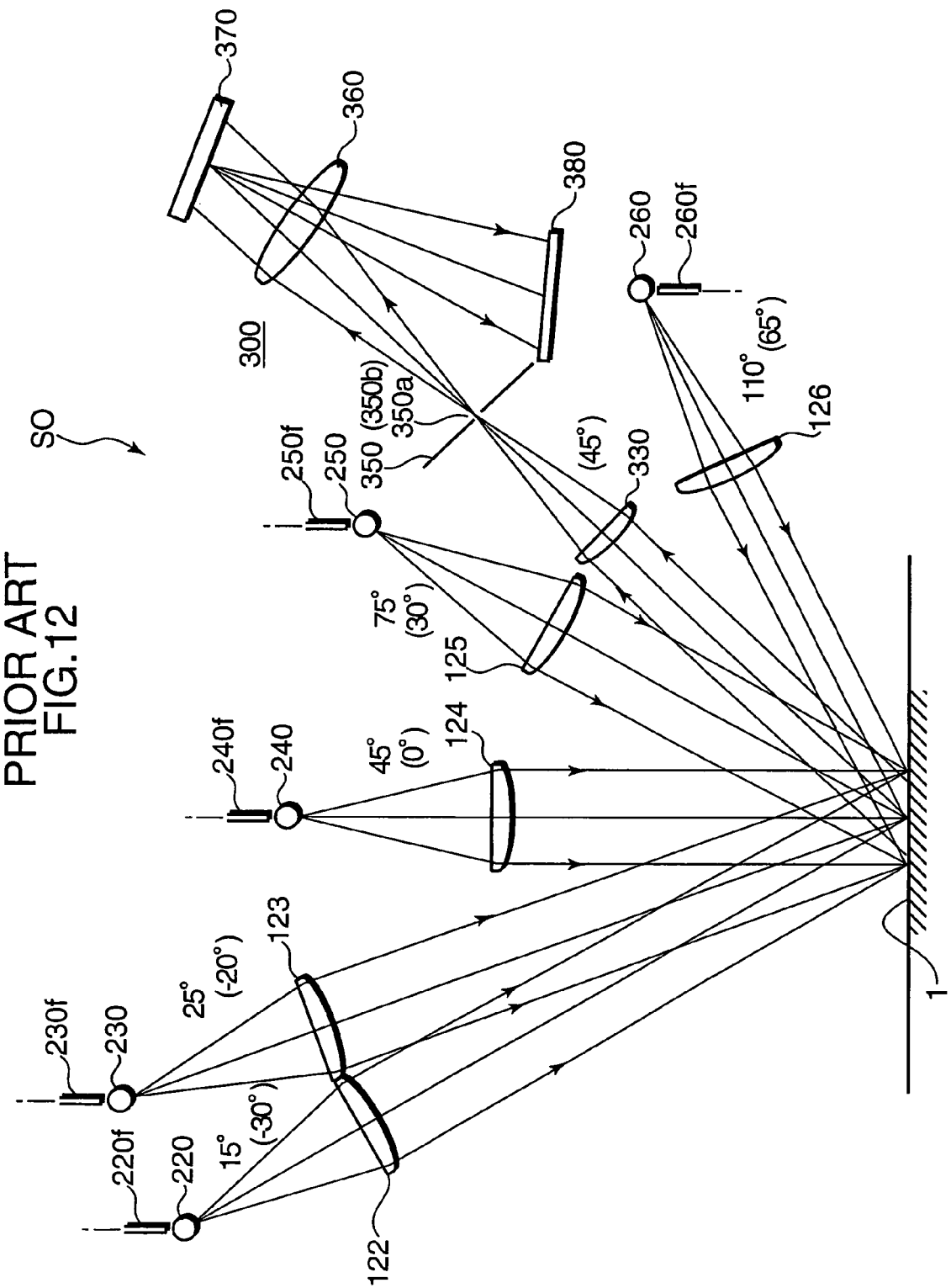

PRIOR ART
FIG.13A
PRIOR ART
FIG.13B
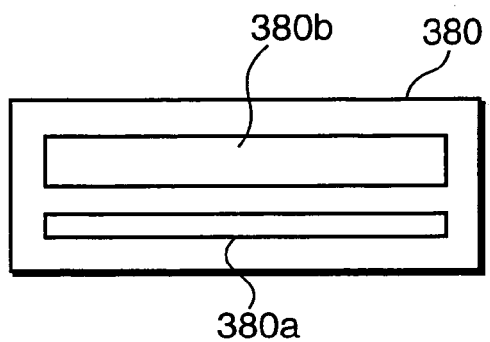
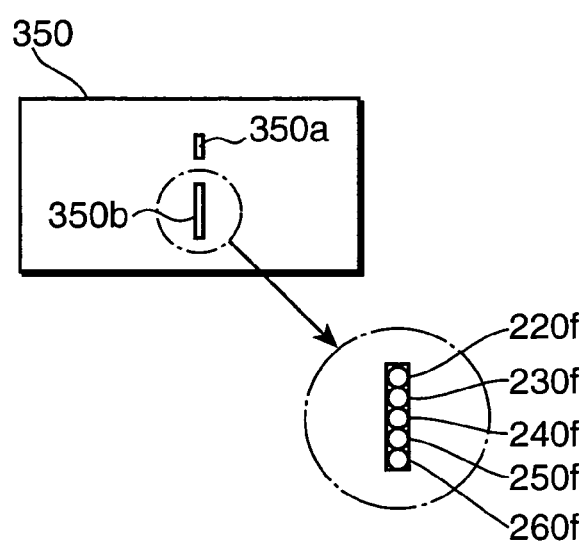

US 7,369,244 B2

OPTICAL MEASURING APPARATUS, ILLUMINATION SYSTEM, AND LIGHT DETECTING SYSTEM

This application is based on Japanese Patent Application No. 2004-335759 filed on Nov. 19, 2004, the contents of which are hereby incorporated by reference.

BACKGROUND OF THE INVENTION

1. Field of the Invention

The present invention relates to an optical measuring apparatus including a multi-angle colorimeter for measuring in different illuminating or viewing directions a special effect coating such as a metallic coating and a pearl-color coating having a property that different colors are provided depending on an illuminating direction or a viewing direction, as well as an illumination system and a light detecting system for use in the optical measuring apparatus.

2. Description of the Related Art

In a metallic coating or a pearl-color coating used for a coating of an automotive vehicle or the like, flakes of aluminum or mica called bright materials are contained in a coating, which provides a metallic effect or a pearl effect. Such an effect is provided because contribution of the bright materials to reflection characteristics varies depending on an illuminating direction and a viewing direction. Optical measuring apparatus having a multi-angle geometry of the type in which illumination light is projected in a multitude of directions and reflected light is detected in one direction, or the type in which illumination light is projected in one direction and reflected light is detected in a multitude of directions are used as optical measuring apparatus for evaluating or measuring the color of the metallic coating and the pearl-color coating having the characteristic as mentioned above.

FIG. 12 is a schematic illustration showing an optical system S0 of a conventional optical measuring apparatus, in which illumination light is projected in a multitude of directions and reflected light is detected in one direction. The optical system S0 has five light sources 220, 230, 240, 250 and 260 arranged at five different angular positions as five illuminators, and a light detecting unit 300 arranged at a specified angular position as a single light detecting system. The five illuminators and the light detecting system each is constituted of a dioptric or refractive optical system. As shown by the brackets in FIG. 12, the light detecting direction of the light detecting unit 300 is set at 45 degrees with respect to a normal to an object surface 1, the illuminating directions of the light sources 220, 230, 240, 250 and 260 are respectively set at −30 degrees, −20 degrees, 0 degree, 30 degrees and 65 degrees with respect to the normal to the object surface 1, with the side where the light detecting direction is located with respect to the normal to the object surface being assumed to be positive.

The illuminating direction for causing specular or direct reflection light in the light detecting direction, namely, the specular reflection direction is set at −45 degrees with respect the normal. Accordingly, as shown in FIG. 12, the angles of the respective illuminating directions of the light sources 220, 230, 240, 250 and 260 with respect to the specular reflection direction or the anti-specular reflection angles are 15 degrees, 25 degrees, 45 degrees, 75 degrees, and 110 degrees. The optical system S0 embraces requirements on a geometry [15 degrees, 45 degrees, 110 degrees], and a geometry [25 degrees, 45 degrees, and 75 degrees], wherein the respective angles represent angles of illuminators with respect to the aspecular angles, as recommended by ASTM E2194 and DIN6175-2, 2001, which are the two primary standards for color evaluation of metallic coating and pearl coating.

An operation of an optical measuring apparatus equipped with the optical system S0 is described. First, the light sources 220, 230, 240, 250, and 260 are successively turned on by unillustrated controlling means. Light beams emanated from the respective light sources 220, 230, 240, 250, and 260 are collimated into parallel beams by collimator lenses 122, 123, 124, 125, and 126, and the object surface 1 is illuminated by the illumination beams from the respective illuminating directions. The beams reflected by the object surface 1 at 45 degrees with respect to the normal (45 degree anormal), namely, object beams are converged on an object slit 350a in a slit plate 350 through a light receiving lens 330 of the light detecting unit 300. The converged object beams are incident onto a diffraction grating 370 as parallel beams after passing through a focusing lens 360 for dispersive reflection with respect to each wavelength component. Thereafter, the dispersed and reflected beams are converged by the focusing lens 360, and incident onto an object array 380a in a sensor array 380 shown in FIG. 13A, with a dispersed image of the object slit 350a shown in FIG. 13B being formed thereon.

Also, parts of output beams from the light sources 220, 230, 240, 250, and 260 are guided to incident ends of monitoring optical fibers 220f, 230f, 240f, 250f, and 260f as reference beams to monitor fluctuation of illumination beams emitted from the five illuminators 220, 230, 240, 250, and 260. Exit ends of the monitoring fibers 220f, 230f, 240f, 250f, and 260f are arrayed on a reference slit 350b in a slit plate 350 shown in FIG. 13B. Similarly to the object beams, the reference beams successively emitted from the exit ends of the monitoring fibers 220f, 230f, 240f, 250f, and 260f are incident onto a reference array 380b in the sensor array 380, with a dispersed image of the reference slit 350b being formed thereon.

Signals indicative of spectral intensities of the object beams and the reference beams that have been incident onto the object array 380 are processed by an unillustrated processing circuit as spectral intensity data, which is sent to unillustrated controlling/computing means. The controlling/computing means calculates spectral reflection coefficients of the object surface in the respective reflection directions based on the spectral intensity data of the object beams and the reference beams by using illumination beams in the respective illuminating directions, and converts the spectral reflection coefficients into a color value or the like, according to needs.

In the aforementioned optical system S0, it is necessary to radially arrange the illuminators each having a long axial length from the corresponding light source to the object surface. Also, it is necessary to set the length from the object surface to the respective collimator lenses sufficiently long to avoid interference between the adjoining collimator lenses arranged in two different angular positions. The following is an example of the latter drawback. Let it be assumed that in the arrangement shown in FIG. 12, the illumination area on the object surface 1 has 15 mm in size. Then, the distance from the object surface 1 to the collimator lens 122 (123) must be 80 mm or more to avoid interference of the collimator lenses 122 and 123 in the space between the two illuminators having the angles of 15 degrees and 25 degrees with respect to the specular reflection direction (15 degree aspecular and 25 degree aspecular). In an actual arrangement, since lens barrels for holding the respective collimator lenses therein are provided in the optical measuring apparatus, it is necessary to set the distance between the object surface and the respective collimator lenses to such a value that the adjoining lens barrels do not interfere with each other. Consequently, increase in the size of the optical measuring apparatus is unavoidable. If such a large-sized optical measuring apparatus is made portable, an operator may feel difficulty in using the optical measuring apparatus in an actual measurement field.

SUMMARY OF THE INVENTION

In view of the problems residing in the prior art, it is an object of the present invention to provide an optical measuring apparatus which is free from the problems residing in the prior art.

It is another object of the present invention to provide a small size optical measuring apparatus, in which positional constraints regarding an optical system such as an illumination system and a light detecting system including a collimator lens are eliminated, and the optical system is compact in size.

An aspect of the invention is directed to an optical measuring apparatus adapted for use in measuring reflection characteristics of an object surface comprising: an illumination system including a toroidal mirror having a concave reflecting surface formed by circularly rotating a parabolic curve or its approximate curve around an axis with the focal point of the parabolic curve or the substantial light focusing point of the approximate curve forming a focal point arc, and a plurality of light emitters of which light emitting portions are arranged on or in the vicinity of the focal point arc such that the beams emanated from the light emitting portions are reflected by the toroidal mirror in parallel with each other in the direction of a parabolic shape towards the axis in different directions; a light detecting system which detects light beams reflected by the object surface in a specific direction; a controller for controlling the operation of the optical measuring apparatus to successively turn on the illuminators, and detect the light beams reflected by the object surface in respective illuminating directions of the light emitters; and a calculator for calculating the reflection characteristics of the object surface in the respective illuminating directions.

Another aspect of the invention is directed to an optical measuring apparatus adapted for use in measuring reflection characteristics of an object surface comprising: an illumination system which illuminates a surface of the object in a specific direction; a light detecting system including a toroidal mirror having a concave reflecting surface formed by circularly rotating a parabolic curve or its approximate curve around an axis with the focal point of the parabolic curve or the substantial light focusing point of the approximate curve forming a focal point arc, and a plurality of light detectors arranged at a plurality of angular positions on or in the vicinity of the focal point arc to detect beams reflected in different directions by the object surface; a controller for controlling the operation of the optical measuring apparatus to turn on the illumination system and receive the outputs of respective light detectors, and a calculator for calculating the reflection characteristics of the object surface in the respective detecting directions in accordance with the outputs of the light detectors.

Yet another aspect of the invention is directed to an illumination system for illuminating an object surface comprising: a toroidal mirror having a concave reflecting surface formed by circularly rotating a parabolic curve or its approximate curve around an axis with the focal point of the parabolic curve or the substantial light focusing point of the approximate curve forming a focal point arc; and a plurality of light beam emitters arranged on or in the vicinity of the focal-point arc, wherein light beams emanated from the light emitters are reflected by the toroidal mirror in parallel with each other due to the parabolic curve of the toroidal mirror and directed in different directions towards the object surface due to the arc curve of the toroidal mirror.

Still another aspect of the invention is directed to a light detecting system for detecting light beams reflected by an object surface comprising: a toroidal mirror having a concave reflecting surface formed by circularly rotating a parabolic curve or its approximate curve around an axis with the focal point of the parabolic curve or the substantial light focusing point of the approximate curve forming a focal point arc; and a plurality of light detectors arranged on or in the vicinity of the focal point arc, wherein beams reflected by the object surface in different directions are reflected by the toroidal mirror for incidence onto the light detectors.

These and other objects, features and advantages of the present invention will become more apparent upon reading of the following detailed description along with the accompanying drawings.

BRIEF DESCRIPTION OF THE DRAWINGS

FIG. 4 is a sectional view taken in a direction perpendicular to a measurement plane, showing an arrangement of a light detecting system in FIG. 2.

FIG. 12 is an illustration showing an optical system of a conventional optical measuring apparatus of the type in which light is projected in a multitude of directions and detected in one direction.

FIG. 13A is a front view of a sensor array in the arrangement of FIG. 12.

FIG. 13B is a front view of an object slit in the arrangement of FIG. 12.

DETAILED DESCRIPTION OF THE PREFERRED EMBODIMENTS

Figure 1A:
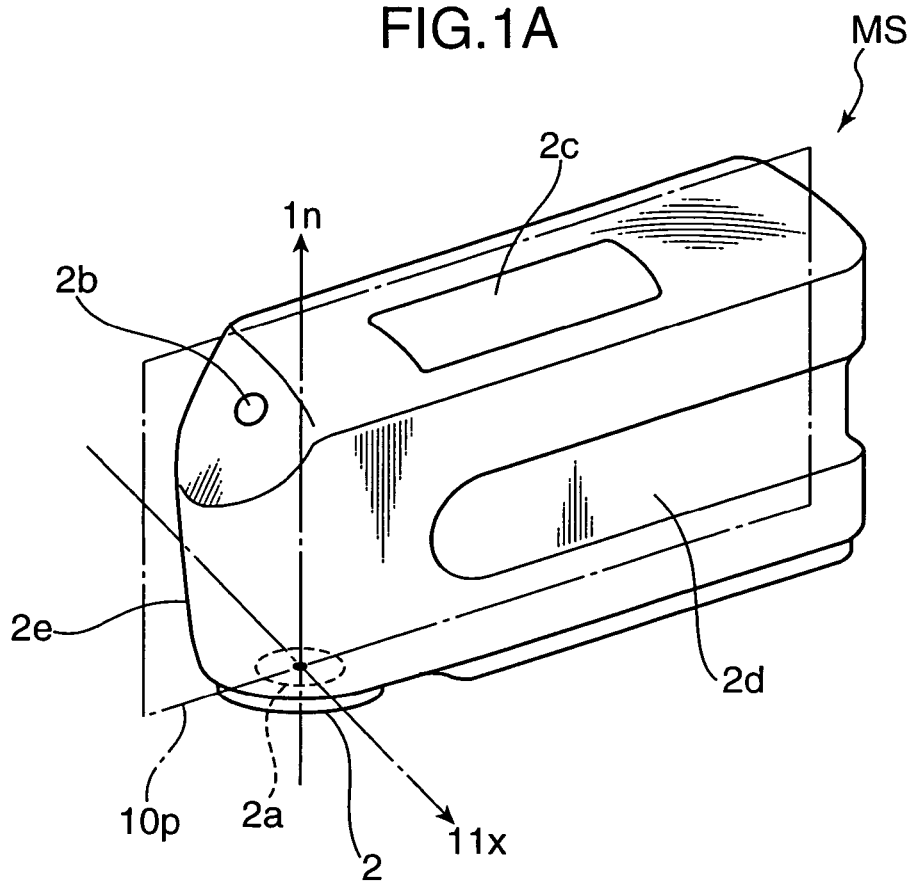
FIG. 1A is a perspective view schematically showing an external appearance of an optical measuring apparatus according to an embodiment of the present invention.

In the following, embodiments of the invention are described referring to the drawings.

(Description on Entire Arrangement of Multi-angle Colorimeter)

FIG. 1A is a perspective view schematically showing an external appearance of a multi-angle colorimeter MS, as an example of the optical measuring apparatus embodying the invention. The multi-angle colorimeter MS has an elongated box-shaped casing body 2e constituting a main body of the colorimeter MS for housing therein various components of the colorimeter MS including optical systems such as an illumination system and a light detecting system, which will be described later. A part of a bottom wall of the casing body 2e constitutes a measurement surface 2. The measurement surface 2 is formed with a measurement opening 2a of a certain shape e.g. an elliptical shape. Also, the casing body 2e has a viewfinder section 2b for allowing an operator to view a surface 1 of a targeted measurement object d, a display section 2c such as an LCD, which is arranged on a top surface of the casing body 2e for displaying measurement results and the like, and a grip portion 2d for allowing the operator to grip the casing body easily for handling of the colorimeter MS.

Figure 1B:
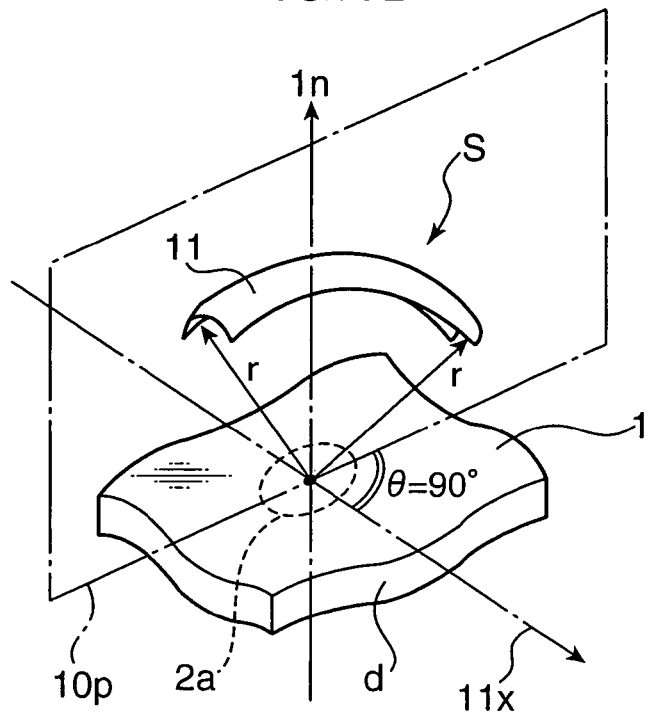
FIG. 1B is a perspective view schematically showing essential parts of an internal arrangement of the optical measuring apparatus shown in FIG. 1A.

As shown in FIG. 1B, the multi-angle colorimeter MS is operated in such a manner that color measurement and evaluation of the object surface 1, for instance, color measurement and evaluation for color management of metallic coatings are performed by setting the measurement opening 2a of the multi-angle colorimeter MS to oppose the surface 1 of the measurement object d. In the case where the measurement object d is an automotive body applied with a metallic coating or a pearl-color coating, the object surface 1 corresponds to the surface of the coating on the automotive body.

In this embodiment, a toroidal mirror 11 is equipped in an optical system S of the multi-angle colorimeter MS to illuminate the object surface by a reflection optical system which contributes to reduction of the size of the multi-angle colorimeter MS. The toroidal mirror in this embodiment is a concave mirror constructed such that curvatures are different from each other in two directions which are orthogonal to each other. In this embodiment, the toroidal mirror 11 having the following features is used. Specifically, as shown in FIG. 1B, the curvature in the direction parallel with an imaginary measurement plane 10p is circular or arc-shape with its center being an axis 11x which lies on an object surface orthogonal to the measurement plane. The radius of the arc is r on the measurement plane. The curvature in the direction orthogonal to the measurement plane 10p is parabolic as will be described in more detail later. In short, the reflective plane of the toroidal mirror 11 has a concave shape formed by locus of a parabolic curve rotated circularly around the axis 11x.

Figure 2:
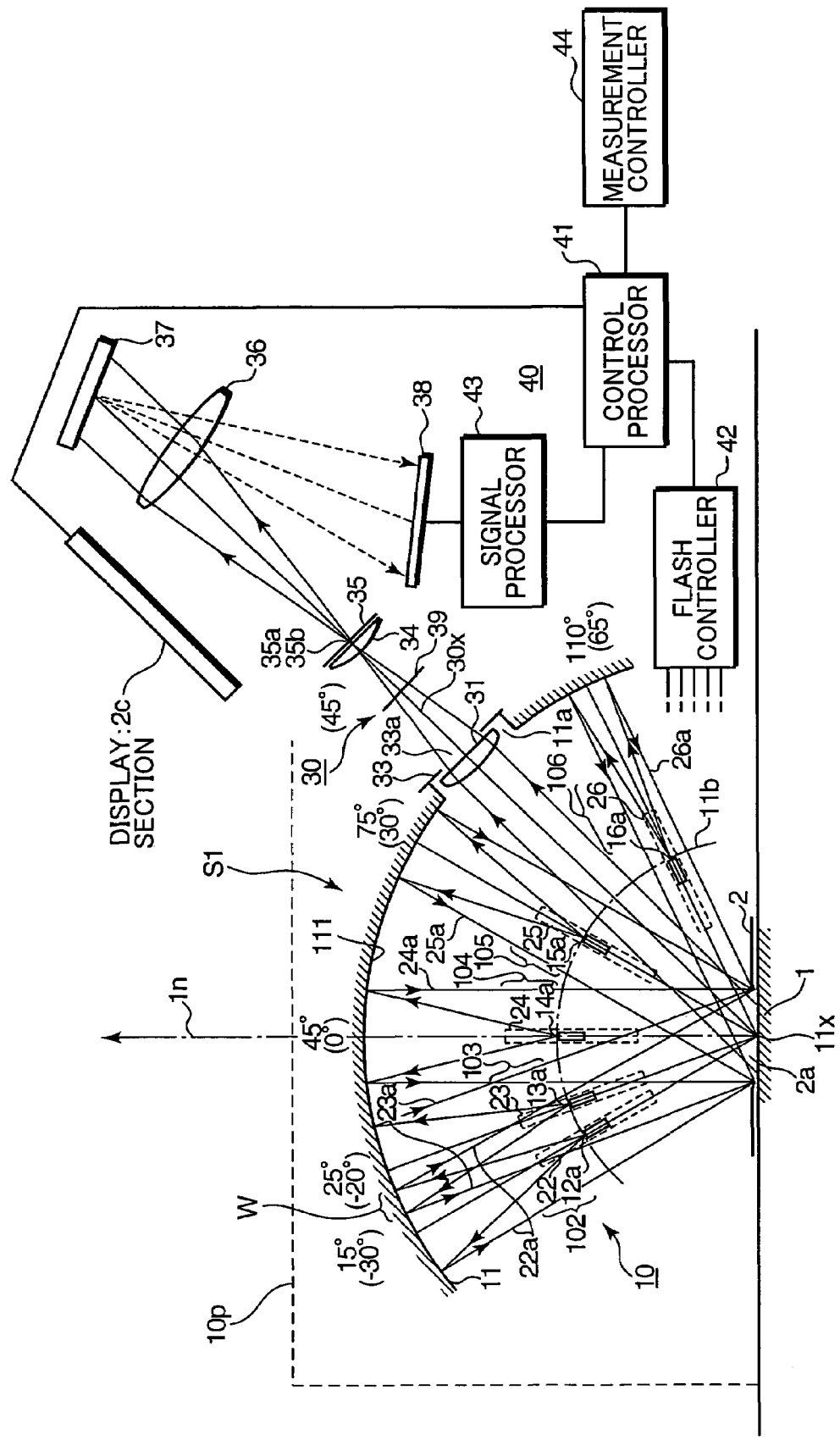
FIG. 2 is an illustration showing an internal arrangement of the optical measuring apparatus.
Figure 3:
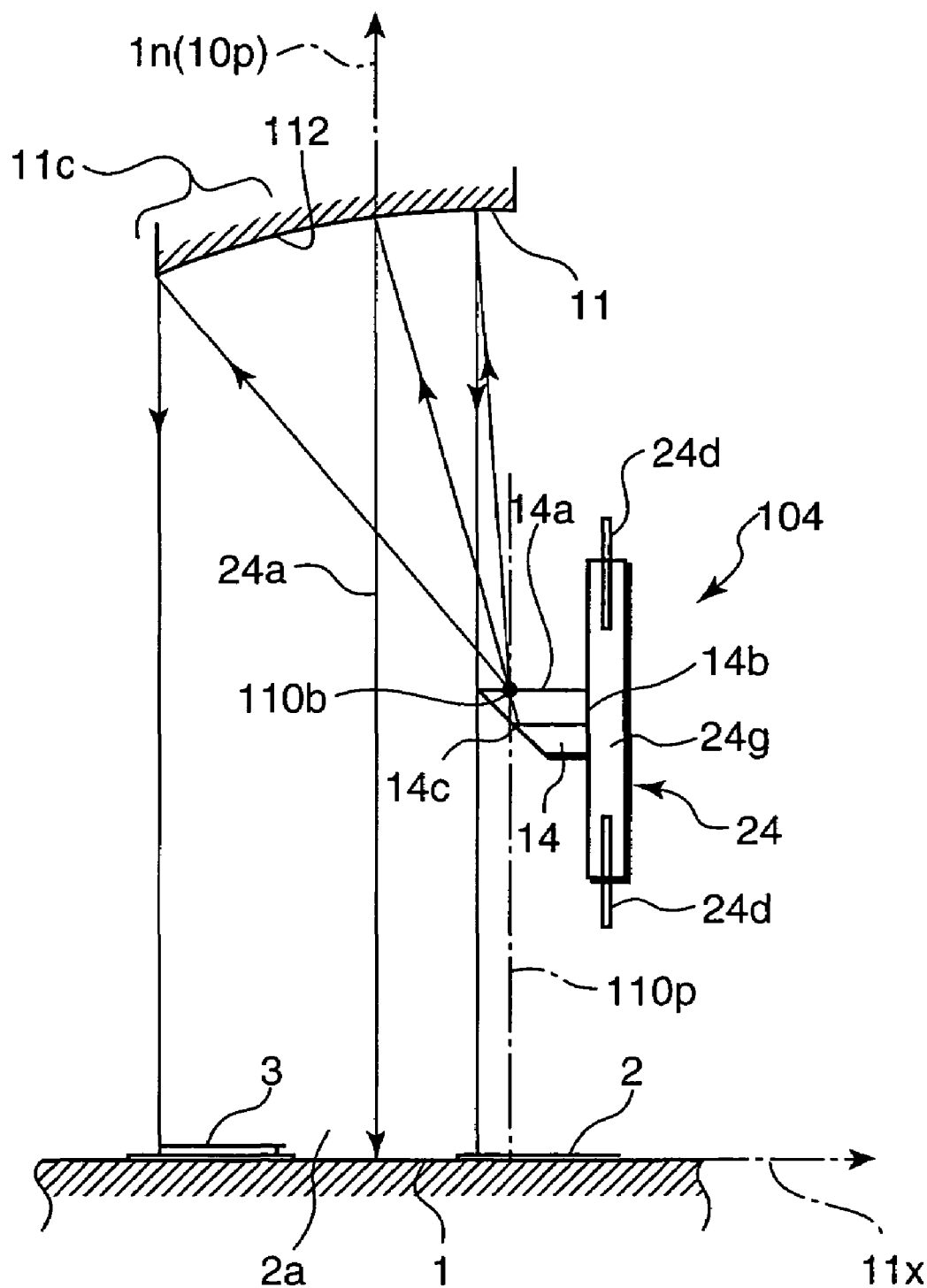
FIG. 3 is a partial sectional side view of the optical measuring apparatus taken in a direction perpendicular to a normal to an object surface shown in FIG. 2.

FIG. 2 is an illustration showing an internal arrangement of the multi-angle colorimeter MS in this embodiment. FIG. 3 is a partial side view of the calorimeter MS in section taken along the normal line 1n in FIG. 2. The multi-angle colorimeter MS has, as an optical system S1, an illumination system 10 for illuminating the object surface 1 of the measurement object d disposed to oppose the measurement opening 2a of the measurement surface 2, a light detecting system 30 for measuring spectral characteristics of the beams reflected by the object surface 1 which has been illuminated by the illumination system 10, and a controller/calculator 40 serving as a control processor for controlling the illumination system 10 and the light detecting system 30 to calculate reflection characteristics of the object surface 1 based on the measurement data outputted from the light detecting system 30 for output. In FIG. 2, the measurement plane 10p is depicted by the dashed lines, and the axis 11x is depicted as the solid dot in view of the fact that the axis 11x extends in a direction perpendicular to the plane of FIG. 2. Those measurement plane 10p and the axis 11x shown in FIG. 2 respectively correspond to the same shown in FIG. 1

(Illumination System)

The illumination system 10 includes the toroidal mirror 11, and first, second, third, fourth, and fifth illuminators 102, 103, 104, 105, and 106 which are respectively arranged at −30 degrees, −20 degrees, 0 degree, 30 degrees, and 65 degrees with respect to the normal line 1n, as shown in the parentheses in FIG. 2. This positional arrangement satisfies the geometry requirements: [15 degrees, 45 degrees, and 110 degrees] and [25 degrees, 45 degrees, and 75 degrees], as recommended by ASTM E2194 and DIN6175-2, 2001, which are the two primary standards in color evaluation of metallic coating and pearl-color coating, wherein the respective angles represent angles of respective illuminators with respect to an aspecular angle. According to these standards, a multi-angle calorimeter which satisfies the above requirements is recommended as a multi-angle calorimeter MS for color evaluation of metallic coating and pearl-color coating.

The arc of toroidal mirror 11 extends in the direction parallel to the measurement plane 10p, substantially covering the first, the second, the third, the fourth and the fifth illuminators 102, 103, 104, 105 and 106 disposed at the respective angular positions of −30 degrees, −20 degrees, 0 degree, 30 degrees, and 65 degrees with respect to the normal line 1n. Also, as shown in FIG. 3, the toroidal mirror 11 is parabolic in the direction parallel to the axis 11x. A focal point 110b of the parabolic surface 112 is set at a position substantially half of the radius r of the arc surface 111 and outside of a plane which is proximate to a perimeter of the measurement opening 2a, namely, a perimeter for defining a predetermined measurement area on the object surface 1, and which is parallel to the measurement plane 10p.

The axis of the parabola of the surface 112 extends through the focal point 110b to the axis 11x. In this arrangement, illumination beams or reflection beams emanated from the focal point in the respective illuminating/reflecting directions on the measurement plane 10p are reflected by the parabolic surface in parallel with the direction of the radius of the arc (the portion of a circular curve on the concave plane of the toroidal mirror), thereby regulating the direction of the illumination beams and enabling to perform high-precision measurement for an object surface applied with a metallic coating or pearl coating and having a high directional dependency. The position of the focal point 110b can be arbitrarily set by setting the curved surface 112 appropriately. It is, however, desirable to set the focal point 110b at a position on or proximate to the measurement plane 10p, as shown in FIG. 3, to achieve parallelism of illumination beams or reflection beams in the respective directions on the measurement plane 10p.

As the parabola is rotated around the axis 11x to form the concave plane of the toroidal mirror, the trajectory of the focal point 110b of the parabola is an arc 11b, or the path swept by the focal point 110b is described as the arc 11b with its center being the axis 11x and its radius being a half of the radius r of the arc where the concave plane traverses the measurement plane as shown in FIG. 2. As mentioned above, the focal point 110b is set on or at a position proximate to the measurement plane 10p, and the curvature of the curved surface 112 is set constant along the circumferential direction of the curved surface 111. Accordingly, the focal-point arc 11b lies on a flat plane 110p (see FIG. 3) which is proximate to the measurement plane 10p and is parallel to the measurement plane 10p.

In the above mentioned embodiment, the toroidal surface has a concave shape formed by locus of a parabolic curve rotated circularly around the axis 11x. In other words, the curved surface 112 is parabolic. Instead, the curved surface may have another shape of curve which is approximate to the parabolic, such as an arc shape approximate to the parabolic. In the latter case, the focal-point arc 11b may be formed by the locus of the substantial light focusing point of the approximate curve forming a focal point arc. The substantial light focusing point may be such a point where the light reflected by the approximate curve surface is focused or concentrated in substance.

The first, the second, the third, the fourth, and the fifth illuminators 102, 103, 104, 105, and 106 are comprised of small right-angle prisms 12, 13, 14, 15, and 16 having exit ends 12a, 13a, 14a, 15a, and 16a, and flash light sources 22, 23, 24, 25, and 26 including xenon lamps disposed proximate to incident ends 12b, 13b, 14b, 15b, and 16b of the small right-angle prisms 12, 13, 14, 15, and 16, respectively. The right-angle prisms in the present embodiment are prisms for deflecting the horizontal incident light at right angle toward their exit surfaces. In FIG. 3, a side view of the right-angle prism 14 and of the flash light source 24 of the third illuminator 104 is illustrated. The flash light source 24 is a light source comprised of a pair of electrodes 24d, 24d arranged at opposite ends of an elongated xenon tube 24g. The flash light source 24 is a source for generating illumination beams for illuminating the object surface 1. The incident end 14b of the right-angle prism 14 is in contact with an intermediate part of the xenon tube 24g, so that light emanated from the flash light source 24 is incident onto the right-angle prism 14 through the incident end 14b.

The illumination beams incident onto the right-angle prism 14 are deflected by an internal reflection surface 14c, and directed toward the toroidal mirror 11 through the exit end 14a. The exit end 14a is disposed at a position on the focal point of the curved surface 112 of the toroidal mirror 11, namely, on the focal-point arc 11b. The exit end 14a has a sufficiently small exit area, as compared with the focal length of the curved surface 112. In this arrangement, since the exit area of the exit end 14a is sufficiently small as compared with the focal length of the curved surface 112, illumination beams of high parallelism can be projected onto the object surface 1. The first, the second, the fourth, and the fifth illuminators 102, 103, 105, and 106 have the same arrangements as that of the third illuminator 104 as mentioned above.

As shown in FIG. 2, illumination beams 22a, 23a, 24a, 25a, and 26a emanated from the first, the second, the third, the fourth, and the fifth illuminators 102, 103, 104, 105, and 106 are reflected by the toroidal mirror 11, and the object surface 1 is illuminated with the illumination beams 22a, 23a, 24a, 25a, and 26a which are made parallel to the radial lines extending in the measurement plane 10p at their respective angles of −30 degrees, −20 degrees, 0 degree, 30 degrees, and 65 degrees with respect to the normal line 1n. As an alternative, the illuminators may be disposed to directly oppose the toroidal mirror 11. In this embodiment, however, since illumination beams are allowed to go out through the exit ends 12a, 13a, 14a, 15a, and 16a of the small right-angle prisms 12, 13, 14, 15, and 16, as mentioned above, there is no likelihood that the flash light sources 22, 23, 24, 25, and 26 may block the illumination beams 22a, 23a, 24a, 25a, and 26a. In this arrangement, since the focal-point arc 11b can be set proximate to the measurement plane 10p, aberration of the toroidal mirror 11 can be suppressed, and parallelism of the illumination beams 22a, 23a, 24a, 25a, and 26a can be improved.

A reference plane 3 is provided in proximity to the object surface 1 to monitor fluctuation of intensity of the illumination beams emanated from the first, the second, the third, the fourth, and the fifth illuminators 102, 103, 104, 105, and 106. In this embodiment, the reference plane 3 is disposed adjacent to the object surface 1 in a direction perpendicular to the measurement plane 10p. The toroidal mirror 11 has an extension 11c in the extending direction of the axis 11x to allow the reference plane 3 to be illuminated by the first, the second, the third, the fourth, and the fifth illuminators 102, 103, 104, 105, and 106. In other words, the reference plane 3 adjoining the object surface 1 is illuminated by the illumination beams 22a, 23a, 24a, 25a, and 25a reflected by the extension 11c. In this arrangement, aberration may be slightly increased, since a peripheral portion of the toroidal mirror 11, namely, the extension 11c away from the main portion of the toroidal mirror 11 that has the focal point exactly on the arc 11b is used for illuminating the reference plane 3. However, since the reference plane 3 is provided merely for reference beams, this does not cause a serious drawback.

In the illumination system 10 having the above arrangement, the illumination beams 22a, 23a, 24a, 25a, and 26a emanated from the first, the second, the third, the fourth, and the fifth illuminators 102, 103, 104, 105, and 106 travel through folded optical paths, in which the optical paths are folded by the toroidal mirror 11 for reflecting the illumination beams, which in turn reach the object surface 1. This arrangement remarkably reduces the size of the illumination system 10, as compared with an arrangement in which light sources and collimator lenses are linearly arranged around the object surface. Also, the toroidal mirror 11 has the continuous annular reflection surface. This arrangement allows the adjoining illuminators e.g. the first illuminator 102 (−30°) and the second illuminator 103 (−20°) shown in FIG. 2 to commonly use a portion of the reflection surface of the toroidal mirror 11 indicated by the symbol W in FIG. 2. This arrangement eliminates interference of adjoining collimator lenses, as seen in the conventional arrangement, even if two adjoining illuminators at respective angular positions are arranged proximate to each other, thereby contributing to reduction of the size of the illumination system 10.

(Light Detecting System)

Now, the light detecting system 30 is described referring to FIGS. 2 and 4. The light detecting system 30 includes an objective lens 31, an aperture plate 33, a field lens 34, an incident slit plate 35, a focusing lens 36, a diffraction grating 37, a sensor array 38, and a reference beam restricting plate 39. The light detecting system 30 has an optical axis 30x inclined by 45 degrees with respect to the normal passing the center of the object surface 1 on the measurement plane 10p. The specular or direct reflection angle with respect to the light detecting direction having 45 degrees inclination with respect to the normal is −45 degrees. Accordingly, the angles of the first, the second, the third, the fourth, and the fifth illuminators 102, 103, 104, 105, and 106 having illumination angles of −30 degrees, −20 degrees, 0 degree, 30 degrees, and 65 degrees with respect to the normal are 15 degrees, 25 degrees, 45 degrees, 75 degrees, and 110 degrees respectively with respect to the specular reflection direction of the light detecting direction.

The incident slit plate 35, the focusing lens 36, the diffraction grating 37, and the sensor array 38 constitute a polychromator. Specifically, the focusing lens 36 and the diffraction grating 37 are adapted to generate a dispersed image of a slit 35a and a slit 35b of the incident slit plate 35. The sensor array 38 is disposed at the focusing position of the dispersed image of the incident slit 35a. The polychromator is adapted to simultaneously measure the intensities of light at all the wavelengths of the wavelength range to be measured with the light reflected by the object surface 1 being split into beams of the respective wavelengths and detected by the sensor array 38 to generate spectral data depending on the spectral intensities of the reflected beams.

The objective lens 31 is arranged in an opening 11a, which is formed on the toroidal mirror 11 at 45 degrees with respect to the normal, to converge on the incident slit plate 35 the reflected beams traveling along the optical axis 30x. Specifically, as shown in FIG. 4, the objective lens 31 converges the beams reflected by the object surface 1 and the reference plane 3 with the reflection angle of 45 degrees with respect to the normal (45 degree anormal) onto the incident slit plate 35 disposed on a focal plane of the objective lens 31. The object surface 1 and the reference plane 3 are integrally illuminated by the illumination system 10. The beam reflected by the object surface is hereinafter, referred to as "object beams 1c" and the beam reflected by the reference plane is referred to as "reference beams 3c".

The aperture plate 33 has an aperture 33a for passing beams, and is arranged near a back face of the objective lens 31. The aperture plate 33 is adapted to restrict the diameters of the object beams 1c and the reference beams 3c to respective predetermined sizes. The dimension of the aperture 33a is appropriately set in accordance with the dimensions of the object beams 1c and the reference beams 3c to be restricted.

Figure 5A:
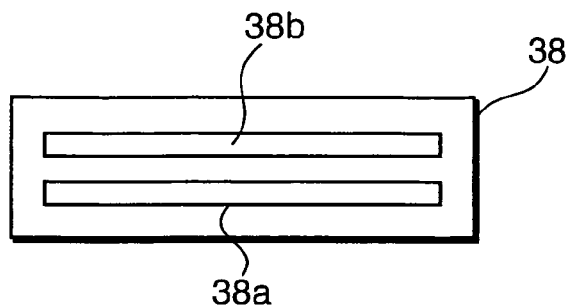
FIG. 5A is a front view of a sensor array.
Figure 5B:
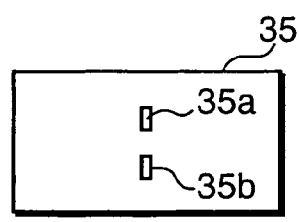
FIG. 5B is a front view of an object slit.

The incident slit plate 35 is formed with the object slit 35a and the reference slit 35b juxtaposed to each other, as shown in FIGS. 4 and 5B. These slits 35a and 35b function as incident slits of the polychromator. Specifically, the object beams 1c converged by the objective lens 31 are guided as converged object beams 1c' to the object slit 35a, and the reference beams 3c are guided as converged reference beams 3c' to the reference slit 35b.

The focusing lens 36 is adapted to collimate the object beams 1c (or object reflected beams) and the reference beams 3c (or reference reflected beams which have been diffusively passed through the object slit 35a and the reference slit 35b, into parallel beams which in turn are guided to the diffraction grating 37. The diffraction grating 37 is adapted to disperse and reflect the parallel beams guided by the focusing lens 36. The parallel beams are dispersed and reflected by the diffraction grating 37 for every wavelength component. The dispersed and reflected beams are converged by the focusing lens 36, and focused on the sensor array 38.

The sensor array 38 outputs signals indicating respective spectral intensities of the object beams 1c and the reference beams 3c to a signal processor 43, which will be described later. As shown in FIG. 5A, the sensor array 38 includes an object array 38a and a reference array 38b. The object array 38a and the reference array 38b are respectively constituted of photo diode arrays of e.g. 40 pixels arrayed in a section of a predetermined size, which are defined in accordance with the sizes of the object slit 35a and the reference slit 35b. The dispersed image of the object slit 35a is formed on the object array 38a, and the dispersed image of the reference slit 35b is formed on the reference array 38b.

The field lens 34 is disposed immediately in front of the incident slit plate 35, namely, on the side of the surface of the incident slit plate 35 opposing the objective lens 31. The field lens 34 functions as a member for forming an optical image of the aperture 33a of the aperture plate 33 at the position of the focusing lens 36. By arranging the field lens 34 at the aforementioned position, all the object beams 1c passing through the object slit 35a and all the reference beams 3c passing through the reference slit 35b are incident onto the focusing lens 36 and the diffraction grating 37, thereby forming the dispersed images on the object array 38a and the reference array 38b. In this arrangement, spectral characteristics of the object beams 1c and the reference beams 3c can be efficiently measured by the common light detecting system.

A reference beam restricting plate 39 is arranged between the incident slit plate 35 and the objective lens 31 to partly block the converged reference beams 3c' in FIG. 4. In the optical system S1 of this embodiment where the object surface 1 and the reference plane 3 are arranged adjoining to each other, the reference beam restricting plate 39 is arranged to minimize the optical path length of the light detecting system 30. This is described in detail by taking a numerical example.

Referring to FIG. 4, the following relational expression is established:

$$b = a \cdot D/d \quad (1)$$

where D represents a distance, on the object surface 1 (reference plane 3), between the optical axis 1x of the object beam 1c and the optical axis 3x of the reference beam 3c, d represents a distance between the object slit 35a and the reference slit 35b, a represents a distance between the incident slit plate 35 and the objective lens 31, and b represents a distance between the object surface 1 (reference plane 3) and the objective lens 31.

Assuming that the diameter of the measurement opening 2a, namely, of a measurement area 1a is 12 mm, and the diameter of the reference plane 3, namely, of a reference area 3a is 8 mm, then, it is required to set the distance D to at least about 12 mm to keep the object beam 1c from overlapping the reference beam 3c in light of the fact that if the object beam 1c is overlapped with the reference beam 3c, it is impossible to accurately monitor the reference beam 3c. The distance D is obtained by implementing the equation (1). If the distance d between the object slit 35a and the reference slit 35b is 3 mm, and the distance a between the incident slit plate 35 and the objective lens 31 is 25 mm, then, the distance b between the object surface 1 (reference plane 3) and the objective lens 31 is 100 mm, which is a relatively long distance.

In view of the above, in this embodiment, the reference beam restricting plate 39 is arranged between the incident slit plate 35 and the objective lens 31 at such a position as to block substantially half of the converged reference beams 3c' that is away from the converged object beams 1c'. In other words, the reference beam restricting plate 39 is adapted to prevent the beams reflected by the object surface 1 from being incident onto the reference slit 35b in the incident slit plate 35. By providing the reference beam restricting plate 39, the reference area 3a on the reference plane 3 has a semi-circular shape, as shown in FIG. 4, with a diametrically extending straight side of the reference area 3a facing the circular measurement area 1a on the object surface 1. The area of the reference area 3a is reduced to half by blocking of the reflected beams corresponding to the other semi-circular area thereof by the distance D. In this way, the circles of the measurement area 1a and the reference area 3a are partly overlapped with each other, in place of defining the measurement area 1a and the reference area 3a as individual circular areas which do not overlap or do not proximate to each other, which resultantly requires the distance D=12 mm. The reference beam restricting plate 39 is used to block part of the reference beams 3c which is supposed to cause overlapping of the reference area 3a with the measurement area 1a, so that the incidence of the part of the reference beams 3c do not affect measurement afterwards. By providing the reference beam restricting plate 39, the distance D can be reduced from 12 mm to 8 mm, and consequently, the distance b can be reduced from 100 mm to 66 mm. This arrangement enables to remarkably shorten the optical path length of the light detecting system 30. The reference beam restricting plate 39 is arranged at such a position that does not interfere with incidence of the converged object beams 1c' onto the objective lens 31, namely, at a position that does not block incidence of the object beams 1c.

Figure 6A:
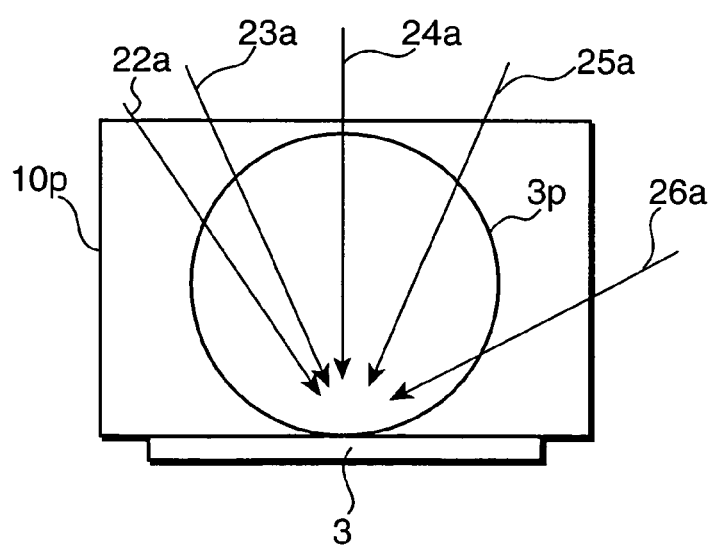
FIGS. 6A and 6B are illustrations showing reflection characteristics of an anisotropic diffusive reflector.
Figure 6B:
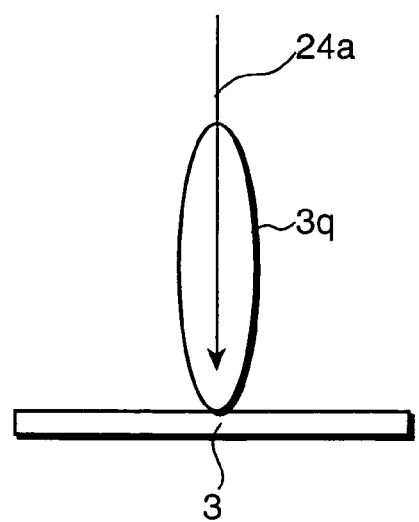

As the area of the reference area 3a is reduced to half by disposing the reference beam restricting plate 39, amount of reference beams for monitoring is decreased. In view of this, it is desirable to arrange a reflector having an anisotropic diffusion characteristic as shown in FIGS. 6A and 6B, as the reference plane 3. Specifically, the anisotropic diffusion reflector has characteristics such that, as shown in FIG. 6A, incident illumination beams 22a, 23a, 24a, 25a, and 26a are diffused and reflected in the direction of the measurement plane 10p with large diffusion/reflection angles to form diffusive reflection beams 3p, and as shown in FIG. 6B, the incident illumination beams 22a, 23a, 24a, 25a, and 26a are diffused and reflected in a direction orthogonal to the measurement plane 10p with small diffusion/reflection angles to form diffusive reflection beams 3q. Use of the anisotropic diffusion reflector as the reference plane 3 enables to allow the illumination beams 22a, 23a, 24a, 25a, and 26a to be efficiently incident onto the light detecting system 30 for obtaining reference beams required for monitoring. An example of the anisotropic diffusion reflector is, for instance, an elliptical profile light shaping diffuser (LSD) produced by Physical Optics Corporation (U.S.A.).

In the light detecting system 30 having the above arrangement, since the reference plane 3 is juxtaposed to the object surface 1 in the direction orthogonal to the measurement plane 10p, similarity between the illumination beams 1c and the reference beams 3c is increased. This arrangement enables to perform high-precision measurement, while correcting fluctuation of intensity of illumination beams to be projected on the object surface 1. Also, use of the reference beam restricting plate 39 enables to shorten the distance b between the object surface 1 and the objective lens 31 which is necessary to isolate the object beams 1c from the reference beams 3c, thereby contributing to reduction of the size of the light detecting system. Further, spectral characteristics of the object beams 1c and the reference beams 3c can be measured by the common light detecting system 30 by providing the field lens 34. Particularly, in the case that the optical system S1 of the type in which illumination light is projected in a multitude of directions and detected in one direction is used as in this embodiment, the reference beams 3c can be monitored by the light detecting system 30 which is commonly used with all the illuminators arranged at the respective angular positions without providing the monitoring optical fibers 220f, 230f, 240f, 250f, and 260f for reference, as in the conventional art. This arrangement enables to eliminate various problems accompanied by use of the optical fibers such that the optical fibers are susceptible to a temperature change or that a space is necessary for housing the optical fibers.

(Control Processor)

Referring back to FIG. 2, the controller/calculator 40 is described. The controller/calculator 40 is adapted to calculate reflection characteristics of the object surface 1 based on measurement data outputted from the light detecting system 30. The controller/calculator 40 comprises a control processor 41 including a central processing unit (CPU) and a memory, a flash controller 42, the signal processor 43, a measurement controller 44, and the display section 2c.

The control processor 41 sends, to the respective parts of the calorimeter MS, control signals to control a measurement operation of the colorimeter MS for measuring the color of the object surface 1. Specifically, upon receiving a measurement start signal from the measurement controller 44, the control processor 41 outputs, to the flash controller 42, a drive signal in accordance with an operation sequence to control flash firing of the flash light sources 22, 23, 24, 25, and 26. Upon receiving spectral intensity signals indicating spectral intensities of the object beams 1c and of the reference beams 3c, the signal processor 43 outputs spectral intensity data to the control processor 41. The control processor 41, in turn, calculates a spectral reflection coefficient with respect to each of the illuminating directions, converts the spectral reflection coefficients into a color value or other index according to needs, and outputs the converted value to the display section 2c for display.

The flash controller 42 generates a control signal for causing the flash light sources 22, 23, 24, 25, and 26 of the first, the second, the third, the fourth, and the fifth illuminators 102, 103, 104, 105, and 106 to successively emit flashlight, based on the drive signal sent from the control processor 41.

The signal processor 43 calculates spectral reflection characteristics of the object surface 1, namely, obtains spectral intensity data, based on intensities of the reflection beams which were emanated from the illumination system 10, and reflected by the object surface 1 and the reference plane 3. The light detecting system 30 detects the spectral intensity signals of the object beams 1c and the reference beams 3c. Specifically, the signal processor 43 calculates spectral reflection characteristics with reference to the respective illuminating directions of the first, the second, the third, the fourth, and the fifth illuminators 102, 103, 104, 105, and 106 by using the spectral intensity signals outputted from the sensor array 38. The signal processor 43 may be composed of a signal processing circuit including a current-voltage conversion circuit, a feedback resistor, a multiplexer, a variable gain amplifier, and an analog-to-digital converter.

The measurement controller 44 is adapted to control an overall operation of the multi-angle colorimeter MS to output, to the control processor 41, a measurement start signal in accordance with a measurement menu designated by the user for execution of the measurement. The display section 2c is adapted to display measurement result data such as a color value, a graph, a measurement menu, and the like.

The operation of the multi-angle colorimeter MS having the above configuration is described briefly. First, when a measurement start signal is generated by the measurement controller 44, the control processor 41 sends a drive signal to the flash controller 42, which, in turn, causes the flash light sources 22, 23, 24, 25, and 26 of the first, the second, the third, the fourth, and the fifth illuminators 102, 103, 104, 105, and 106 to successively emit flashlight. The illumination beams emanated from the respective flash light sources 22, 23, 24, 25, and 26 are reflected by the toroidal mirror 11 and projected onto the object surface 1 and the reference plane 3.

The above light behavior is described in more detail by taking an example of the third illuminator 104 shown in FIG. 3. After the illumination beams are incident onto the incident end 14b of the small right-angle prism 14, the illumination beams change their directions by reflection on the internal reflection surface 14c, and travel through the exit end 14a toward the toroidal mirror 11. The beams are reflected by the toroidal mirror 11, collimated into the parallel illumination beams 24a, and are projected onto the object surface 1 and the reference plane 3. The operations of the first, the second, the fourth, and the fifth illuminators 102, 103, 105, and 106 are the same as that of the third illuminator 104 as mentioned above.

Of the object beams 1c and the reference beams 3c, beams that are reflected parallel with a radius of 45 degree anormal direction and are parallel with the measurement plane 10p, are detected by the light detecting system 30. Specifically, the object beams 1c and the reference beams 3c are respectively converged on the object slit 35a and on the reference slit 35b in the incident silt plate 35 after passing through the object lens 31. Before being converged on the incident slit plate 35, the object beams 1c and the reference beams 3c pass through the aperture 33a in the aperture plate 33, and a portion of the reference beams 3c that are to pass through the semi-circular area=are blocked by the reference beam restricting plate 39.

The object beams 1c and the reference beams 3c respectively passing through the object slit 35a and the reference slit 35b are collimated into parallel beams by the focusing lens 36, and are guided to the diffraction grating 37 for dispersion and reflection with respect to each wavelength component. The dispersed and reflected beams are converged by the focusing lens 36, and focused on the sensor array 38. Since the field lens 34 is arranged on the optical path of the light detecting system 30, all the object beams 1c and all the reference beams 3c respectively passing through the object slit 35a and the reference slit 35b are incident onto the focusing lens 36 and onto the diffraction grating 37.

After the incidence of the object beams 1c and the reference beams 3c on the sensor array 38, spectral intensity signals in accordance with the received object beams 1c and the received reference beams 3c are outputted to the signal processor 43. The signal processor 43, then, calculates spectral intensity data of the object surface 1 based on the received spectral intensity signals, calculates a spectral reflection coefficient with respect to each of the illuminating directions based on the spectral intensity data, converts the calculated spectral reflection coefficients into a color value or other index, and outputs the converted value to the display section 2c for display.

(Description on Modifications)

Figure 7:
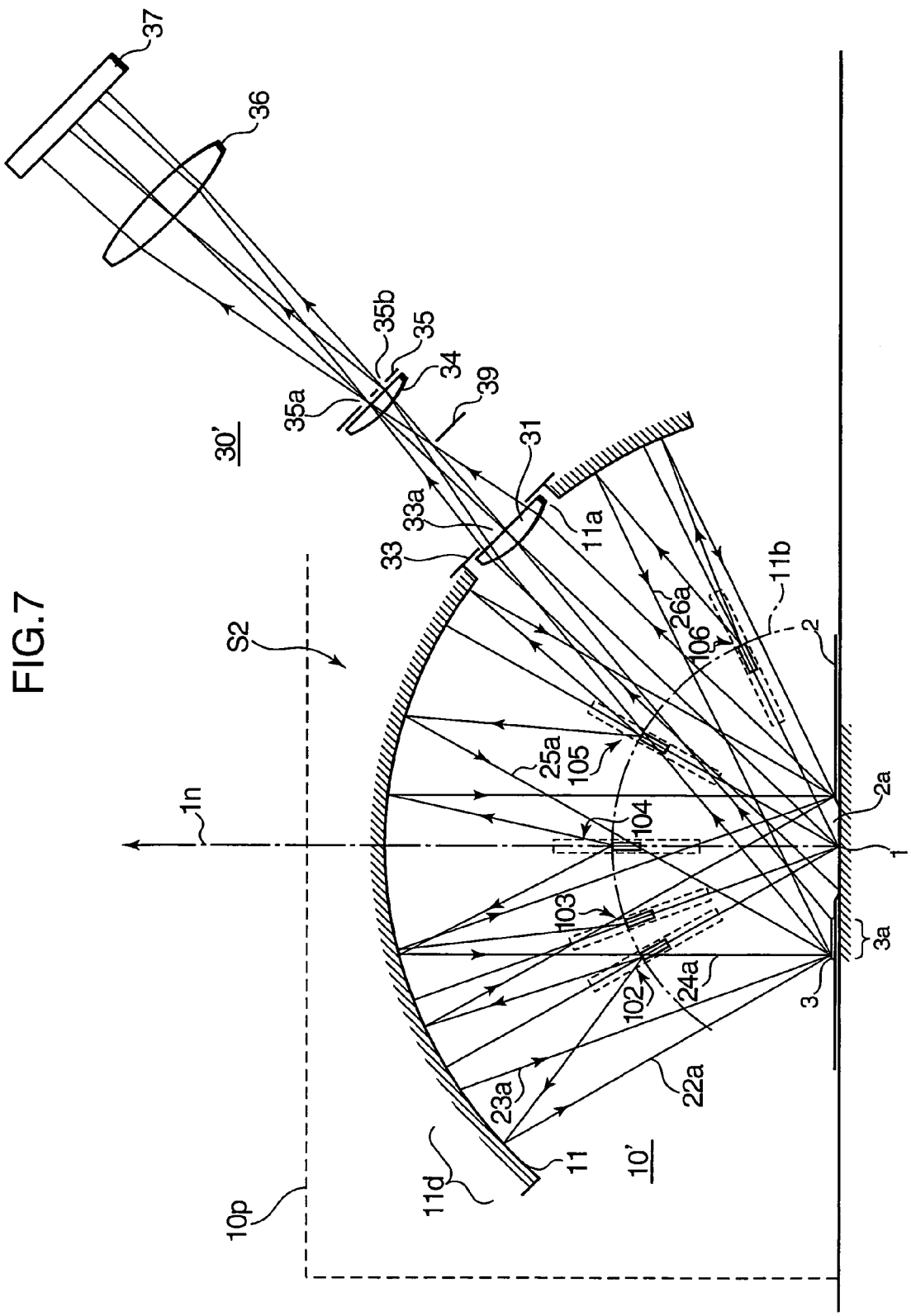
FIG. 7 is an illustration showing a modified optical system.

Modified optical system in which a reference area adjoins an object surface in a direction of a measurement flat plane:

FIG. 7 is an illustration showing a modified optical system to be used in the embodiment of the multi-angle colorimeter MS described above. The optical system S1 in the aforementioned first embodiment is constructed such that the reference plane 3 adjoins the object surface 1 in a direction orthogonal to the measurement plane 10p. According to the modification, the optical system S2 in FIG. 7 is constructed such that a reference plane 3 adjoins an object surface 1 in the direction of a measurement plane 10p. Since the arrangement of the multi-angle calorimeter in the modification is substantially the same as that of the embodiment except for the arrangement of the optical system S2, description thereof is omitted herein.

Referring to FIG. 7, the optical system S2 has an illumination system 10' and a light detecting system 30'. The arrangement of the light detecting system 30' is substantially the same as that of the light detecting system 30 of the first embodiment. In FIG. 7, some of the components are not illustrated. The disposition and the arrangement of first, second, third, fourth, and fifth illuminators 102, 103, 104, 105, and 106 of the illumination system 10' are the same as the corresponding ones of the first embodiment. The manner as to how the illumination beams 22a, 23a, 24a, 25a, and 26a emanated from the first, the second, the third, the fourth, and the fifth illuminators 102, 103, 104, 105, and 106 are reflected on the toroidal mirror 11 and projected on the object surface 1 and the reference plane 3 via respective folded optical paths is the same between the modification and the first embodiment.

In the optical system S2, however, the reference plane 3 adjoins the object surface 1 in the direction of the measurement flat plane 10p. In this arrangement, the illumination beams 22a, 23a, 24a, 25a, and 26a for illuminating the reference plane 3 in the respective illuminating directions are reflected by the same plane of the toroidal mirror 11 as that reflecting the beams for illuminating the object surface 1. This arrangement eliminates provision of an extension 11c, which may increase the size of the toroidal mirror 11 in the direction of the axis 11x, as in the optical system S1 of the first embodiment. The modification is advantageous in reducing the size of the toroidal mirror 11, as compared with the first embodiment. It should be noted, however, that an extension 11d extending in the circumferential direction of the toroidal mirror 11 may be provided to allow the reference plane 3 to be illuminated with the illumination beam 22a emanated from the first illuminator 102 arranged at 15 degrees with respect to the specular reflection direction.

In the optical system S2, since the reference plane 3 or a reference area 3a, and the object surface 1 are adjacent to each other in the direction of the measurement plane 10p, as shown in FIG. 7, it is required that an object slit 35a and a reference slit 35b in an incident slit plate 35 of the light detecting system 30' be formed adjacent to each other in the direction of the measurement plane 10p. In other words, the incident slit plate 35, a focusing lens 36, a diffraction grating 37, and a sensor array 38 constituting a polychromator are arranged at respective angular positions displaced by 90 degrees with respect to the corresponding ones in the optical system S1 about an optical axis 30x. Similarly to the optical system S1, in the optical system S2, a reference beam restricting plate 39 is arranged between the incident slit plate 35 and an objective lens 31 at such a position that does not interfere with incidence of the object beams incident onto the object slit 35a through the objective lens 31. This arrangement enables to block incidence of substantially half of the reference beams and to shorten the distance between the objective lens 31 and the object surface 1.

A compact illumination system can be obtained with use of the optical system S2. Incorporating the illumination system in the multi-angle colorimeter MS further attains reduction of the size of the colorimeter MS.

Figure 8:
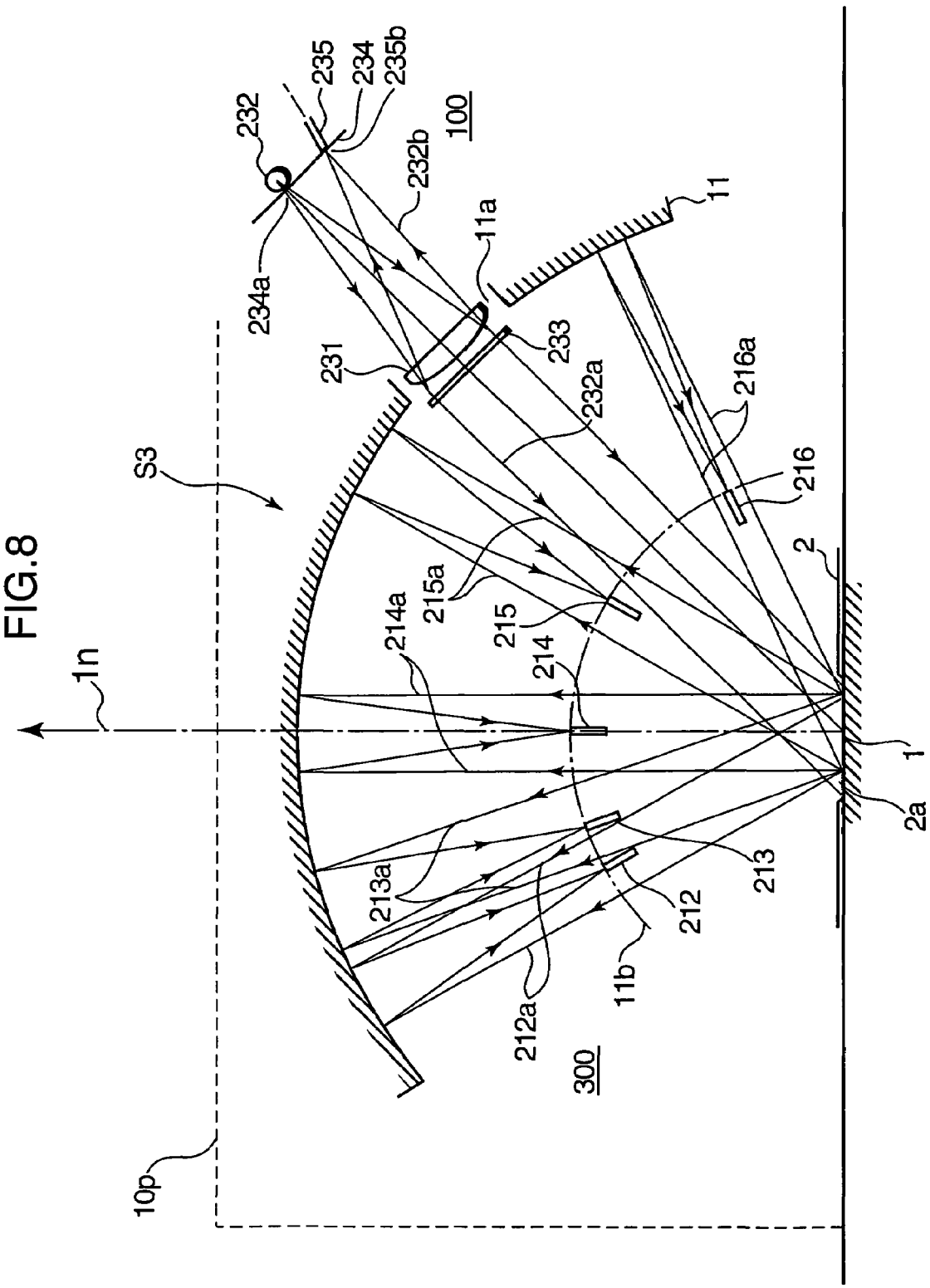
FIG. 8 is an illustration showing another modified optical system.
Figure 9:
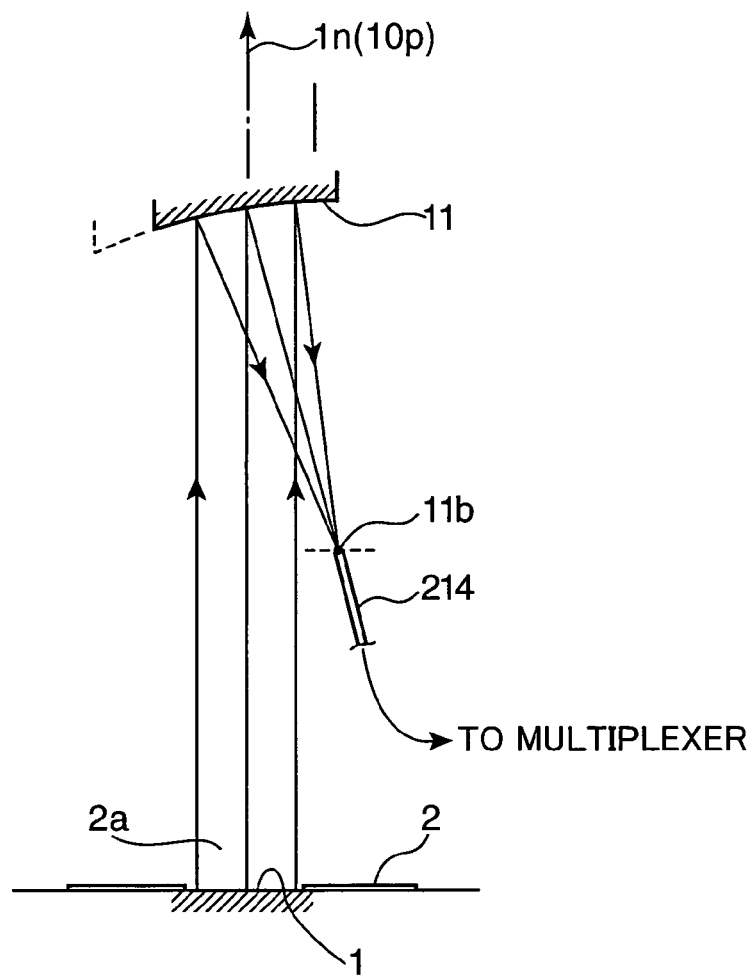
FIG. 9 is a sectional side view of the optical system of FIG. 8 taken in a direction perpendicular to a normal to an object surface in FIG. 8.

Modified optical system of the type in which light is projected in one direction and detected in a multitude of directions:

FIG. 8 is an illustration showing a modified optical system to be used in an embodiment of a multi-angle colorimeter MS according to the present invention. FIG. 9 is a side view in section taken along a normal 1*n* to an object surface 1 in FIG. 8. Whereas the optical system S1 in the first embodiment is of the type in which light is projected in a multitude of directions and detected in one direction, the modified optical system S3 shown in FIG. 8 is of a reverse geometry, in which light is projected in one direction and detected in a multitude of directions.

Referring to FIGS. 8 and 9, the optical system S3 includes an illumination system 100 and a light detecting system 300. The illumination system 100 is comprised of a collimator lens 231 arranged in an opening 11*a* of a toroidal mirror 11 formed at 45 degree with respect to the normal 1*n* (45 degree anormal), an aperture plate 234 disposed at the position of the focal point of the collimator lens 231, and a light source 232 disposed behind an aperture 234*a* in the aperture plate 234. The optical system S3 is also provided with a flat glass 233 arranged near the surface of the collimator lens 231 on the side of the object surface 1 with a certain inclination with respect to the optical axis, and a reference optical fiber 235 having an incident end 235*b* juxtaposed to the aperture 234*a* to monitor fluctuation of intensity of beams emanated from the light source 232.

The light detecting system 300 includes the toroidal mirror 11, and five detecting optical fibers 212, 213, 214, 215, and 216 having incident ends thereof on a focal-point circumference 11*b* of the toroidal mirror 11. The incident ends of the detecting optical fibers 212, 213, 214, 215, and 216 are respectively arranged at positions of −30 degrees, −20 degrees, 0 degree, 30 degrees, and 65 degrees with respect to the normal 1*n* on a measurement flat plane 10*p*.

Figure 10:
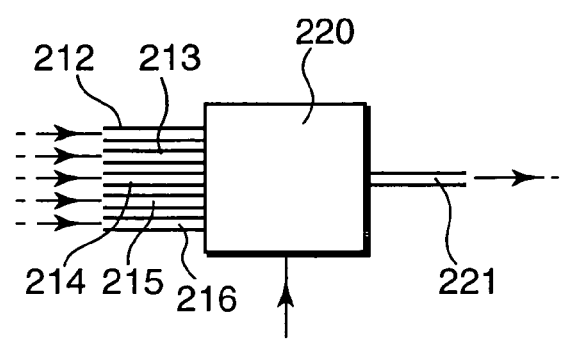
FIG. 10 is a plan view of an exemplified multiplexer.

Exit ends of the detecting optical fibers 212, 213, 214, 215, and 216 are collectively connected to an optical multiplexer 220 shown in FIG. 10. The optical multiplexer 220 is controlled by a control signal from an unillustrated controller/calculator, and has a function of optically connecting the exit ends of the detecting optical fibers 212, 213, 214, 215, and 216 to an output optical fiber 221 one by one sequentially. The exit end of the output optical fiber and the exit end of the reference optical fiber 235 are guided to a polychromator. In case that this arrangement is adopted, the exit end of the output optical fiber and the exit end of the reference optical fiber 235 may be directly connected to an object slit 35*a* and a reference slit 35*b* in an incident slit plate 35, respectively.

An operation of the optical system S3 having the above arrangement is described. Illumination beams emanated from the light source 232 of the illumination system 100 through the aperture 234*a* are collimated into parallel beams 232*a* by the collimator lens 231, and projected onto the object surface 1. Part of the parallel illumination beams 232*a* reflected by the flat glass 233, namely, reference beams 232*b* are converged on the collimator lens 231, and incident onto the reference optical fiber 235 through the incident end thereof juxtaposed to the aperture 234*a*.

Of the beams reflected by the object surface 1 which are illuminated by the parallel beams 232*a*, reflected beams 212*a*, 213*a*, 214*a*, 215*a*, and 216*a* having different reflection directions on the measurement plane 10*p*, are reflected by the toroidal mirror 11, and are incident onto the detecting optical fibers 212, 213, 214, 215, and 216 through the respective incident ends thereof arrayed on the focal-point arc 11*b*. The detecting optical fibers 212, 213, 214, 215, and 216 are sequentially and optically connected to the output optical fiber 221 by the optical multiplexer 220, whereby the reflected beams at reflection angles of −30 degrees, −20 degrees, 0 degree, 30 degrees, and 65 degrees with respect to the normal 1*n* are sequentially guided to the object slit 35*a*. At this time, the reference beams are guided from the reference optical fiber 235 to the reference slit 35*b*. Then, a spectral intensity is measured with respect to each of the reflection angles to the normal 1*n*, namely, with respect to each of the light detecting directions by the polychromator or its equivalent device, and a spectral reflection coefficient is calculated with respect to each of the light detecting directions by a controller/calculator corresponding to the controller/calculator 40 shown in FIG. 2.

The optical system S3 also uses folded optical paths obtained by folding the optical paths of light detectors of the light detecting system 300 by the toroidal mirror 11. Also, use of the toroidal mirror 11 allows the light detectors adjacent to each other to commonly use a portion of the reflection surface of the toroidal mirror 11. This arrangement contributes to size reduction of the light detecting system 300, thereby attaining reduction of size of the multi-angle calorimeter MS incorporated with the light detecting system 300.

Figure 11:
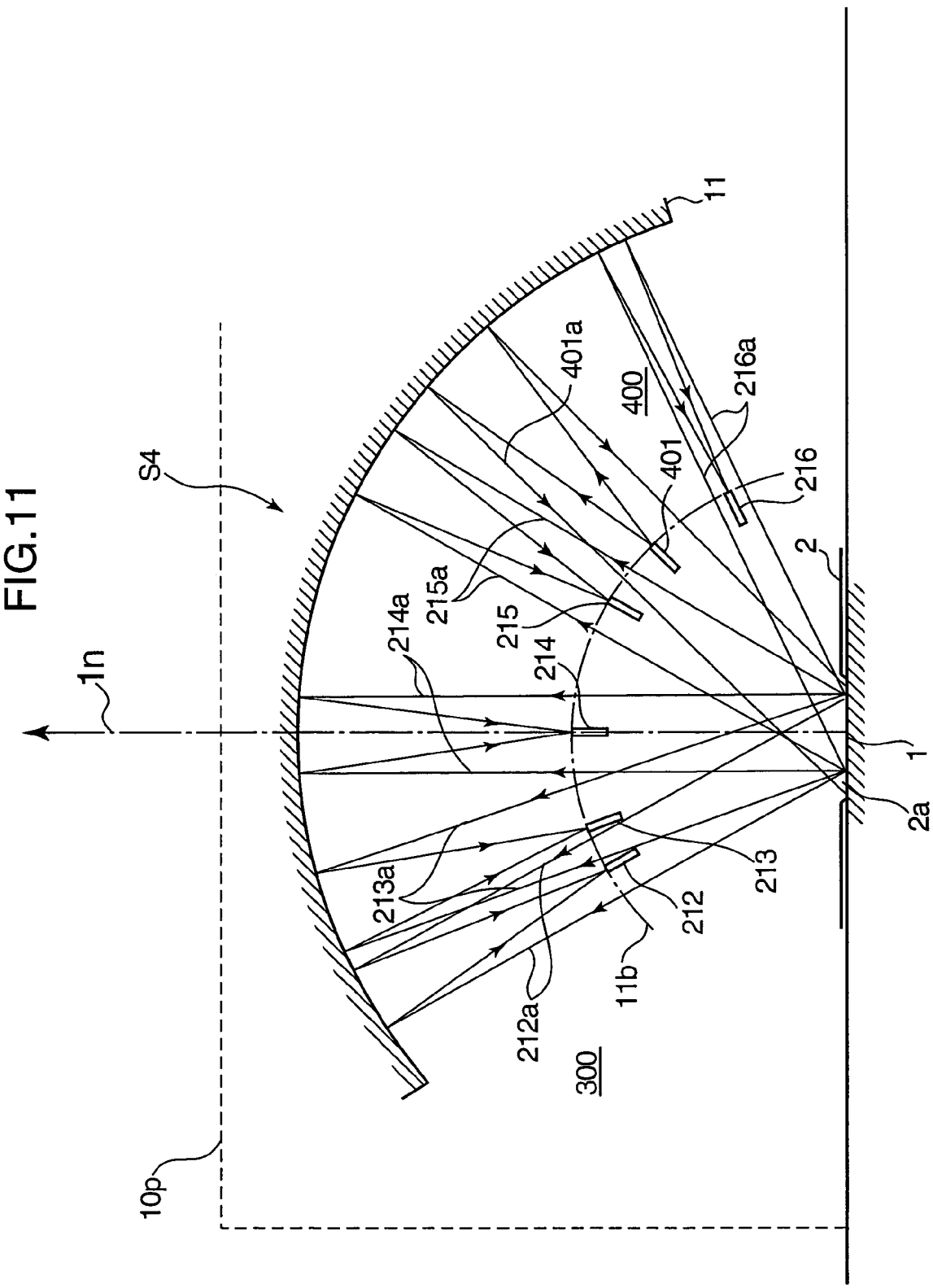
FIG. 11 is an illustration showing yet another modified optical system.

Modified optical system in which a toroidal mirror is commonly used for an illumination system and a light detecting system:

It is possible to modify the optical system S3 shown in FIG. 8 having the arrangement that light is projected in one direction and detected in a multitude of directions, into an optical system S4 shown in FIG. 11, in which an illumination system 400 is composed of a toroidal mirror 11, and an illumination optical fiber 401 having an exit end at a position of 45 degrees with respect to a normal 1*n* on a focal-point arc 11*b* of the toroidal mirror 11 in the similar manner as in the light detecting system 300 in FIG. 8. A light source of a required nature (not shown) is coupled to an incident end of the illumination optical fiber 401 in FIG. 11. In the optical system S4 having the above arrangement, beams emerging from the exit end of the illumination optical fiber 401 are collimated into parallel beams 401*a* which are parallel to the radial direction extending at 45 degrees with respect to the normal 1*n* on a measurement plane 10*p*, so that the parallel beams are projected onto an object surface 1. The arrangement and the operation of the light detecting system 300 for detecting the reflected beams in the respective directions from the object surface 1 are the same as those of the optical system S3 shown in FIG. 8.

The optical system S4 eliminates provision of an additional illumination system composed of lenses and other optical elements. Since the optical path of the illuminator of the illumination system 400 is folded by the toroidal mirror 11 as well as the optical paths of the light detectors in the light detecting system 300, a further small sized multi-angle colorimeter MS can be provided. Also, since the reflection surface of the toroidal mirror 11 can be commonly used by the illumination system 400 and the light detecting system 300 located adjacent to each other, it is possible to measure reflection beams in directions proximate to the illuminating directions.

In FIG. 11, described is the optical system of the type in which light is projected in one direction and detected in a multitude of directions. Alternatively, it is possible to modify the optical system shown in FIG. 2 having the arrangement that light is projected in a multitude of directions and detected in one direction into an optical system, such that a light detecting system is composed of a detecting optical fiber having an incident end at 45 degrees with respect to a normal 1n on a focal-point arc 11b of a toroidal mirror 11.

The embodiment of the invention has been described by taking the example of the multi-angle colorimeter MS. The present invention is applicable to an illumination system or a light detecting system used for various purposes. For instance, in the optical system S1 shown in FIG. 2, or in the optical system S2 shown in FIG. 7, the light detecting system 30 or the light detecting system 30' may be eliminated, and an illumination system may be comprised of plural illuminators arrayed on a focal-point arc 11b of a toroidal mirror 11 to illuminate a first flat plane having a predetermined area. In the altered arrangement, the toroidal mirror 11 is arranged rotationally symmetrical with respect to an axis which is orthogonal to a second flat plane including the normal to the first flat plane and lies on the first flat plane. In this arrangement, beams emanated from the illuminators are reflected on the toroidal mirror 11 as parallel beams, and the first flat plane is illuminated with beams in different directions on the second flat plane.

Further alternatively, it is possible to modify the optical system S3 shown in FIG. 8 in such a manner that the illumination system 100 is eliminated, and a light detecting system is composed of plural light detectors arrayed on a focal-point arc 11b of a toroidal mirror 11 to detect surface emission from a first flat plane having a predetermined area. In this altered arrangement, the toroidal mirror 11 is arranged rotationally symmetrical with respect to an axis which is orthogonal to a second flat plane including a normal to the first flat plane and lies on the first flat plane. This arrangement allows the surface emission from the first flat plane which is illuminated in different directions on the second flat plane to be reflected on the toroidal mirror 11 for detection by the light detecting system.

As described above, an optical measuring apparatus adapted for use in measuring reflection characteristics of an object surface comprises: an illumination system including a toroidal mirror having a concave reflecting surface formed by circularly rotating a parabolic curve or its approximate curve around an axis with the focal point of the parabolic curve or the substantial light focusing point of the approximate curve forming a focal point arc, and a plurality of light emitters of which light emitting portions are arranged on or in the vicinity of the focal point arc such that the beams emanated from the light emitting portions are reflected by the toroidal mirror in parallel with each other in the direction of a parabolic shape towards the axis in different directions; a light detecting system which detects light beams reflected by the object surface in a specific direction; a controller for controlling the operation of the optical measuring apparatus to successively turn on the illuminators, and detect the light beams reflected by the object surface in respective illuminating directions of the light emitters; and a calculator for calculating the reflection characteristics of the object surface in the respective illuminating directions.

In this arrangement, the illumination beams emanated from the illuminators of the illumination system are reflected on the toroidal mirror as parallel beams for projection onto the object surface. Specifically, folded optical paths are constituted, in which the optical paths start around the focal-point circumference of the toroidal mirror, which corresponds to the disposed positions of the illuminators, are folded by the toroidal mirror, and reach the object surface. In this arrangement, as compared with the conventional arrangement shown in FIG. 12, in which the light sources and the collimator lenses are linearly arranged around the object surface, the size of the illumination system can be remarkably reduced. Also, since the toroidal mirror has the continuous annular reflection surface, the reflection surface of the toroidal mirror can be commonly used by the illuminators adjacent to each other. This arrangement eliminates a drawback such as interference of collimator lenses as in the conventional arrangement, even if illuminators at different angular positions are arranged proximate to each other, which contributes to miniaturization of the illumination system.

According to this arrangement, folded optical paths obtained by folding the optical paths of the illuminators by the toroidal mirror are adopted, and use of the toroidal mirror allows the illuminators arranged adjacent to each other to commonly use the reflection surface of the toroidal mirror. This arrangement contributes to remarkable miniaturization of the illumination system, and consequently enables to miniaturize the optical measuring apparatus incorporated with the illumination system.

Preferably, each of the light emitting portions has an area sufficiently small as compared with a focal length of the parabolic curve.

In this arrangement, since the exit area of the each illuminator is sufficiently small as compared with the focal length thereof to the toroidal mirror, illumination beams of high parallelism can be projected onto the object surface.

According to this arrangement, since the illumination beams of high parallelism are projected onto the object surface, reflection characteristics of less measurement error can be obtained.

Preferably, the focal point arc is arranged outside of a plane which is proximate to a perimeter for defining a predetermined measurement area and extends parallel to the measurement area.

In the arrangement where the illuminators are arranged in the vicinity of the focal-point circumference of the toroidal mirror, the illuminators are arranged outside of the plane which is proximate to the perimeter for defining the measurement area on the object surface and is parallel to the measurement flat plane. This arrangement enables to keep the illuminators from blocking the parallel illumination beams generated by reflection on the toroidal mirror.

According to this arrangement, since the illuminators do not block the parallel illumination beams generated by reflection on the toroidal mirror, the object surface can be securely illuminated with the illumination beams of a sufficient light amount, thereby enabling to acquire accurate reflection characteristics.

Preferably, each of the light emitters includes a light exit located on the focal-point arc, a light source disposed at a position away from the light exit, and a light guiding member for guiding the beams of the light source to the light exit.

In this arrangement, since the focal-point circumference of the toroidal mirror is defined on the flat plane parallel to the measurement flat plane and proximate thereto, the illumination beams emanated from the illuminators constitute beams close to the focal-point circumference. This arrangement raises parallelism of the illumination beams or the reflection beams in the respective directions on the measurement flat plane. Also, since the light guiding member is provided, there is no likelihood that the illuminators may block the illumination beams even if the focal-point circumference is arranged proximate to the measurement flat plane.

According to this arrangement, parallelism of the illumination beams or the reflection beams in the respective directions on the measurement flat plane can be raised. Also, since the light guiding member is provided, there is no likelihood that the illuminators may block the illumination beams even if the focal-point circumference is arranged proximate to the measurement flat plane. This arrangement enables to accurately acquire reflection characteristics.

Preferably, the optical measuring apparatus further comprises a reference plane adjoining a measurement area in the direction of the parabolic curve of the toroidal mirror for monitoring light beams projected to the measuring area, wherein the toroidal mirror includes an extension extending in the direction of the parabolic curve to reflect the light from the light emitter towards the reference plane.

In this arrangement, the illumination beams from the illuminators are reflected on the extension of the toroidal mirror for projection onto the reference plane, which is provided adjoining the object surface in the direction orthogonal to the measurement flat plane to know information regarding the illuminators for generating illumination beams.

According to this arrangement, since the reference plane is provided adjoining the object surface in the direction orthogonal to the measurement flat plane, similarity between the illumination beams and the reference beams is raised, and measurement can be performed by securely referring to and correcting information regarding fluctuation of intensity of the illumination beams to be projected onto the object surface. In the case where the object surface and the reference plane are arranged proximate to each other, the size increase of the conventional illumination system is inevitable in light of interference of collimator lenses. However, in this arrangement, the extension is formed in the extending direction of the axis of the rotational symmetry of the toroidal mirror to illuminate the reference plane with the illumination beams. This arrangement eliminates the size increase of the illumination system. Accordingly, the advantages by arranging the reference plane and the object surface adjacent to each other are provided, yet securing remarkable size reduction of the illumination system.

Preferably, the optical measuring apparatus further comprises a reference plane adjoining a measurement area in the direction of the arc curve of the toroidal mirror for monitoring light beams projected to the measuring area, wherein the toroidal mirror includes an extension extending in a circular direction of the toroidal mirror to illuminate the reference plane.

In this arrangement, the illumination beams from the illuminators are reflected on the extension of the toroidal mirror for projection onto the reference plane, which is provided adjoining the object surface in the direction of the measurement flat plane to know information regarding the illuminators for generating illumination beams.

According to this arrangement, since the extension formed in the circumferential direction of the toroidal mirror is adapted to illuminate the reference plane adjoining the object surface in the direction of the measurement flat plane, the advantages by arranging the reference plane and the object surface adjacent to each other are provided, yet securing remarkable size reduction of the illumination system.

An optical measuring apparatus adapted for use in measuring reflection characteristics of an object surface according to another aspect of the invention comprises: an illumination system which illuminates a surface of the object in a specific direction; a light detecting system including a toroidal mirror having a concave reflecting surface formed by circularly rotating a parabolic curve or its approximate curve around an axis with the focal point of the parabolic curve or the substantial light focusing point of the approximate curve forming a focal point arc, and a plurality of light detectors arranged at a plurality of angular positions on or in the vicinity of the focal point arc to detect beams reflected in different directions by the object surface; a controller for controlling the operation of the optical measuring apparatus to turn on the illumination system and receive the outputs of respective light detectors, and a calculator for calculating the reflection characteristics of the object surface in the respective detecting directions in accordance with the outputs of the light detectors.

In this arrangement, the reflection beams from the object surface, namely, parallel beam components, are incident onto the toroidal mirror, reflected thereon, and incident onto the light detectors arranged in the vicinity of the focal-point circumference of the toroidal mirror. In other words, folded optical paths are constituted, in which the optical paths start from the object surface, are folded by the toroidal mirror, and reach the light detectors arranged in the vicinity of the focal-point circumference of the toroidal mirror. This is a so-called reverse geometry, in which the light detecting system and the illumination system are arranged in a reverse manner to those in the aforementioned arrangement. This arrangement enables to remarkably reduce the size of the light detecting system. Also, since the toroidal mirror has the continuous annular reflection surface, the reflection surface of the toroidal mirror can be commonly used by the illuminators adjacent to each other, and there is no likelihood that interference of optical components may occur even if the illuminators at different angular positions are arranged proximate to each other, which contributes to miniaturization of the light detecting system.

According to this arrangement, folded optical paths obtained by folding the optical paths of the light detectors by the toroidal mirror are adopted, and use of the toroidal mirror allows the light detectors adjacent to each other at different angular positions to commonly use the reflection surface of the toroidal mirror in the reverse geometry arrangement, which contributes to remarkable miniaturization of the light detecting system. This arrangement enables to miniaturize the optical measuring apparatus incorporated with the light detecting system.

An illumination system for illuminating an object surface according to yet another aspect of the invention comprises: a toroidal mirror having a concave reflecting surface formed by circularly rotating a parabolic curve or its approximate curve around an axis with the focal point of the parabolic curve or the substantial light focusing point of the approximate curve forming a focal point arc; and a plurality of light beam emitters arranged on or in the vicinity of the focal-point arc, wherein light beams emanated from the light emitters are reflected by the toroidal mirror in parallel with each other due to the parabolic curve of the toroidal mirror and directed in different directions towards the object surface due to the arc curve of the toroidal mirror.

According to this arrangement, folded optical paths obtained by folding the optical paths of the illuminators by the toroidal mirror are adopted, and use of the toroidal mirror allows the illuminators adjacent to each other at different angular positions to commonly use the reflection surface of the toroidal mirror. This arrangement contributes to remarkable miniaturization of the illumination system, and consequently enables to miniaturize various measurement equipment incorporated with the illumination system.

A light detecting system for detecting light beams reflected by an object surface according to still another aspect of the invention comprises: a toroidal mirror having a concave reflecting surface formed by circularly rotating a parabolic curve or its approximate curve around an axis with the focal point of the parabolic curve or the substantial light focusing point of the approximate curve forming a focal point arc; and a plurality of light detectors arranged on or in the vicinity of the focal point arc, wherein beams reflected by the object surface in different directions are reflected by the toroidal mirror for incidence onto the light detectors.

According to this arrangement, folded optical paths obtained by folding the optical paths of the light detectors by the toroidal mirror are adopted, and use of the toroidal mirror allows the light detectors adjacent to each other at different angular positions to commonly use the reflection surface of the toroidal mirror. This arrangement contributes to remarkable miniaturization of the light detecting system, and consequently enables to miniaturize various measurement equipment incorporated with the light detecting system.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

What is claimed is:

1. An optical measuring apparatus adapted for use in measuring reflection characteristics of an object surface comprising:
    an illumination system including
        a toroidal mirror having a concave reflecting surface formed by circularly rotating a parabolic curve or its approximate curve around an axis with the focal point of the parabolic curve or the substantial light focusing point of the approximate curve forming a focal point arc, and
        a plurality of light emitters of which light emitting portions are arranged on or in the vicinity of the focal point arc such that the beams emanated from the light emitting portions are reflected by the toroidal mirror in parallel with each other in the direction of a parabolic shape towards the axis in different directions;
    a light detecting system which detects light beams reflected by the object surface in a specific direction;
    a controller for controlling the operation of the optical measuring apparatus to successively turn on the illuminators, and detect the light beams reflected by the object surface in respective illuminating directions of the light emitters; and
    a calculator for calculating the reflection characteristics of the object surface in the respective illuminating directions.

2. The optical measuring apparatus according to claim 1, wherein each of the light emitting portions has an area sufficiently small as compared with a focal length of the parabolic curve.

3. The optical measuring apparatus according to claim 1, wherein the focal point arc is arranged outside of a plane which is proximate to a perimeter for defining a predetermined measurement area and extends parallel to the measurement area.

4. The optical measuring apparatus according to claim 1, wherein
    each of the light emitters includes a light exit located on the focal-point arc, a light source disposed at a position away from the light exit, and a light guiding member for guiding the beams of the light source to the light exit.

5. The optical measuring apparatus according to claim 1, further comprising a reference plane adjoining a measurement area in the direction of the parabolic curve of the toroidal mirror for monitoring light beams projected to the measuring area, wherein the toroidal mirror includes an extension extending in the direction of the parabolic curve to reflect the light from the light emitter towards the reference plane.

6. The optical measuring apparatus according to claim 1, further comprising a reference plane adjoining a measurement area in the direction of the arc curve of the toroidal mirror for monitoring light beams projected to the measuring area, wherein the toroidal mirror includes an extension extending in a circular direction of the toroidal mirror to illuminate the reference plane.

7. An optical measuring apparatus adapted for use in measuring reflection characteristics of an object surface comprising:
    an illumination system which illuminates a surface of the object in a specific direction;
    a light detecting system including
        a toroidal mirror having a concave reflecting surface formed by circularly rotating a parabolic curve or its approximate curve around an axis with the focal point of the parabolic curve or the substantial light focusing point of the approximate curve forming a focal point arc, and
        a plurality of light detectors arranged at a plurality of angular positions on or in the vicinity of the focal point arc to detect beams reflected in different directions by the object surface;
    a controller for controlling the operation of the optical measuring apparatus to turn on the illumination system and receive the outputs of respective light detectors, and
a calculator for calculating the reflection characteristics of the object surface in the respective detecting directions in accordance with the outputs of the light detectors.

8. An illumination system for illuminating an object surface comprising:
    a toroidal mirror having a concave reflecting surface formed by circularly rotating a parabolic curve or its approximate curve around an axis with the focal point of the parabolic curve or the substantial light focusing point of the approximate curve forming a focal point arc; and
    a plurality of light beam emitters arranged on or in the vicinity of the focal-point arc, wherein
    light beams emanated from the light emitters are reflected by the toroidal mirror in parallel with each other due to the parabolic curve of the toroidal mirror and directed in different directions towards the object surface due to the arc curve of the toroidal mirror.

9. A light detecting system for detecting light beams reflected by an object surface comprising:
    a toroidal mirror having a concave reflecting surface formed by circularly rotating a parabolic curve or its approximate curve around an axis with the focal point of the parabolic curve or the substantial light focusing point of the approximate curve forming a focal point arc; and a plurality of light detectors arranged on or in the vicinity of the focal point arc, wherein beams reflected by the object surface in different directions are reflected by the toroidal mirror for incidence onto the light detectors.

* * * * *